Figure 1:
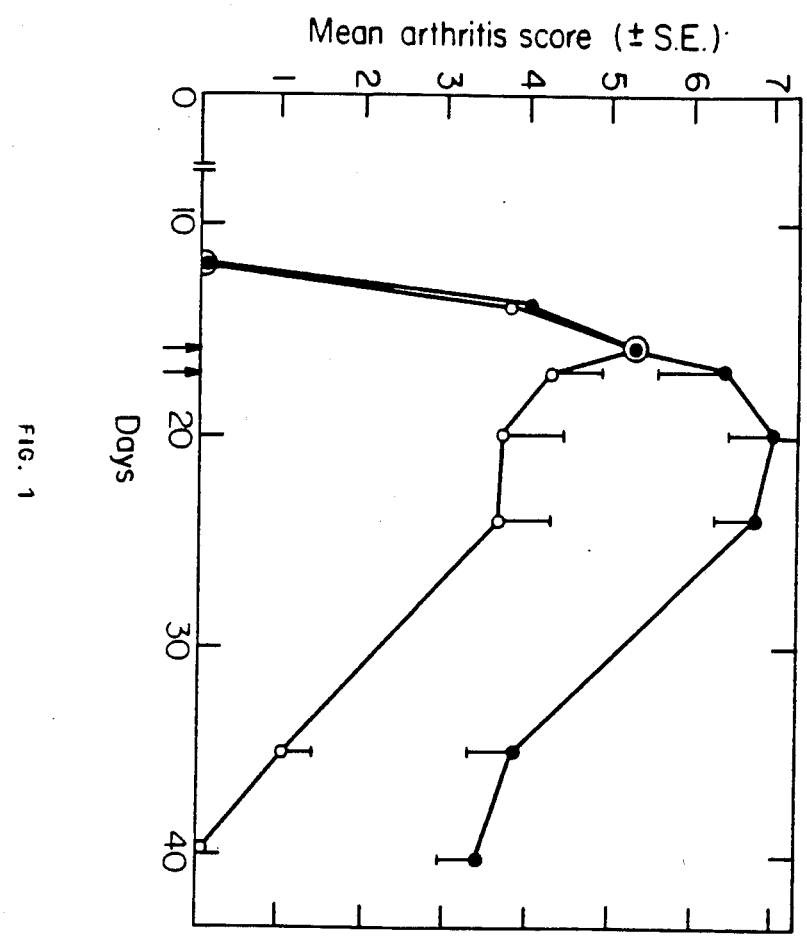

United States Patent [19]

Stanford et al.

[11] Patent Number: 4,716,038

[45] Date of Patent: Dec. 29, 1987

[54] METHODS FOR THE ALLEVIATION OR TREATMENT OF ARTHRITIC DISEASE

[76] Inventors: John L. Stanford, Mill House, Claygate, Marden, Kent, England; Irun R. Cohen, 11, Hankin Street, Rehovot, Israel; Ayala Frenkel, 5, Hanasi Harishon Street, Rehovot, Israel; Joseph Holoshitz, 24, Hiber Street, Petach Tikva, Israel; Willem van Eden, Hooglandse Kerksteeg, 3, N-2312 HR Leiden, Netherlands; Graham A. W. Rook, 27, Glenloch Road, London NW3 4DJ, England

[21] Appl. No.: 817,742

[22] PCT Filed: Apr. 29, 1985

[86] PCT No.: PCT/GB85/00183

§ 371 Date: Feb. 25, 2986

§ 102(e) Date: Feb. 25, 1986

[87] PCT Pub. No.: WO85/05034

PCT Pub. Date: Nov. 21, 1985

[30] Foreign Application Priority Data

Apr. 27, 1984 [IL] Israel .......................................... 71683

[51] Int. Cl.⁴ ...................... A61K 39/02; A61K 35/74
[52] U.S. Cl. ........................................ 424/92; 424/95; 424/195.1

[58] Field of Search ................ 424/95, 195, 92

[56] References Cited

FOREIGN PATENT DOCUMENTS 0045237 2/1982 European Pat. Off. .
2184531 12/1973 France .
2275224 1/1976 France .

OTHER PUBLICATIONS

Jolles et al.–Chem. Abst., vol. 68 (Jun. 1968), p. 112335y.
Bahr et al.–Biol. Abst., vol. 73 (1982), p. 76033.
Watson et al.–Biol. Abst., vol. 69 (1980), p. 2847.
Collins–Infection and Immunity, vol. 20 (May 1978), pp. 430–438.
Rook et al.–Parasite Immunol., vol. 1 (1979), pp. 111 to 115.

Primary Examiner—Sam Rosen
Attorney, Agent, or Firm—Cushman, Darby & Cushman

[57] ABSTRACT

The invention provides pharmaceutical compositions for the alleviation of arthritic diseases. These contain as active ingredient mycobacteria or fractions of these, e.g. obtained by fractionation in certain solvents. The compositions can also be used for vaccinations. There is also provided an assay for the diagnosis of arthritic diseases, and a kit for carrying such an assay.

6 Claims, 3 Drawing Figures

METHODS FOR THE ALLEVIATION OR TREATMENT OF ARTHRITIC DISEASE

The invention relates to preparations for preventing various arthritic afflictions, for alleviating symptoms of arthritic diseases and of other autoimmune diseases, and for their diagnosis.

The novel preparations are based on certain mycobacteria or on certain fractions obtained from mycobacteria. There were also developed certain clones of T-lymphocytes which can be used for diagnostic and therapeutic purposes.

BACKGROUND OF THE INVENTION

Millions of persons are afflicted with chronic forms of arthritis which are thought to involve autoimmunity to constituents of the joints or connecting tissues of the body. These conditions include rheumatoid arthritis, ankylosing spondylitis, Reiter's syndrome and other forms of reactive arthritis. The etiology of these diseases is not known, but previous infection with various microbes seems to act as an inciting circumstance in genetically susceptible individuals. For example, patients with rheumatoid arthritis may show unusual immune reactivity to mycobacterial antigens and immunization with the BCG strain of mycobacteria was found to lead to arthritis in 15 of 150 individuals. Ankylosing spondylitis has been associated with infection by Klebsiella or Yersinia species of bacteria and other cases of arthritis by Salmonella, Snigella, etc. There is no evidence of active infection of joints by these microbes in the vast majority of cases and it has been postulated that microbial infection may trigger an aberrant, autoimmune response of the individual against his own antigens present in the joints.

Adjuvant arthritis (AA) is an experimental model of arthritis inducible by immunizing susceptible strains of rats to Mycobacteria. The disease which develops about 12 days after immunization has many of the features of rheumatiod arthritis and AA has been considered to be a model of rheumatoid arthritis.

SUMMARY OF THE INVENTION

There are provided pharmaceutical preparations for the diagnosis, for the vaccination against, and for the treatment of various autoimmune diseases and especially of arthritic conditions. There exists a family of chronic arthritic conditions such as rheumatoid arthritis, ankylosing spondylitis or Reiter's syndrome which are thought to arise from autoimmune processes in which the joints and other tissues are damaged by the immune system of the patient.

The triggering factors are unknown but it is believed that the infection with certain microbial agents may be important.

Adjuvant arthritis is considered to be an experimental model of autoimmune arthritis inducible in strains of rats by immunizing them to mycobacterial antigens.

According to the present invention there are provided pharmaceutical preparations based on certain mycobacteria and on fractions derived from such mycobacteria.

We have found that various types of mycobacteria, such as Mycobacteria H-37 RA, *M. kansasii, M. vaccae,* and similar strains may be used as such or fractionated by the use of certain solvents to give a precipitate and a water soluble fraction, which latter is suitable for various vaccinations and curative purposes.

Mycobacteria H-37 can be fractionated by the use of an aqueous solution of acetone (66% acetone in water). There is obtained a precipitate (AP) fraction and an acetone soluble (AS) fraction.

The immune response to the AS fraction leads to resistance to adjuvant arthritis; clones of lymphocytes that respond to AS, upon inoculation into naive rats, protect these against subsequent induction of adjuvant arthritis. Inoculation of such clones of lymphocytes into rats suffering from adjuvant arthritis markedly hastens their recovery from the arthritis.

It has been found that clones of T-lymphocytes which cause adjuvant arthritis respond (proliferate) to the AP fraction, but not to the AS fraction.

The SP and the AS fractions are immunologically cross-reactive with proteoglycans of normal joint cartilage, and therefore adjuvant arthritis can be explained as a noxious autoimmune response to AP cross-reactive antigens of proteoglycans. Protection against adjuvant arthritis can be associated with a protective, or disease suppressive response to the AS cross-reactive antigens of proteoglycans.

Diagnostic tests for autoimmune arthritis and similar autoimmune diseases can be based on the different immune reactivity of the tested persons to be AS and the AP fractions of mycobacteria and other bacteria associated with arthritis, or to the AS and AP cross-reactive antigens of proteoglycans. Immunization of patients to AS fractions of mycobacteria and other bacteria associated with arthritic conditions, or to AS cross-reactive antigens or proteoglycans can be used for the prevention of autoimmune arthritis and for the treatment of arthritic diseases.

It has been discovered that certain lines and clones of T-lymphocytes selected for their reactivity to mycobacteria can be used for producing arthritis upon inoculation into irradiated rats.

One line, designated as A2 was found to induce arthritis upon intravenous injection into irradiated rats. The same line, A2 is effective in vaccinating unirradiated rats against subsequent AA induced by active immunization to Mycobacteria.

Cell line A2 has been cloned and there were obtained two distinct clones, designated as A2b and A2c, respectively. A2b causes arthritis but does not vaccinate against it; clone A2c does not cause arthritis but vaccinates against it (see Table 1).

In addition to preventing arthritis, clone A2 can be used to treat AA. FIG. 1 shows the result of an experiment in which rats suffering from AA were inoculated twice (on days 16 and 17 after the induction of disease) with clone A2c, or with a central, irrelevant clone of T-lymphocyte. The rats inoculated with clone A2c went into rapid remission. Six months later the A2c treated rats had normal joints while the control rats had ankylosis and deformities of the paws.

Thus, clones A2b and A2c can be used to identify antigens associated with arthritogenicity or with suppression of arthritogenicity. Both clones respond to whole mycobacteria.

Clone A2b responds to the AP fraction but not to the AS fraction defined above; protective clone A2c responds to AS and only slightly tp AP. Both A2b and A2c respond to cartilage proteoglycan, see Table 2.

Results presented in Table 3 demonstrate that anti-AP and anti-AS antisera recognize cross-reactive antigens in cartilage. AP and AS induce different classes of antibodies, IgG and IgM, respectively, which indicates that these fractions induce functionally different responses. IgG is associated with AP and arthritogenicity while IgM is associated with AS and suppression of arthritogenicity.

Figure 2:
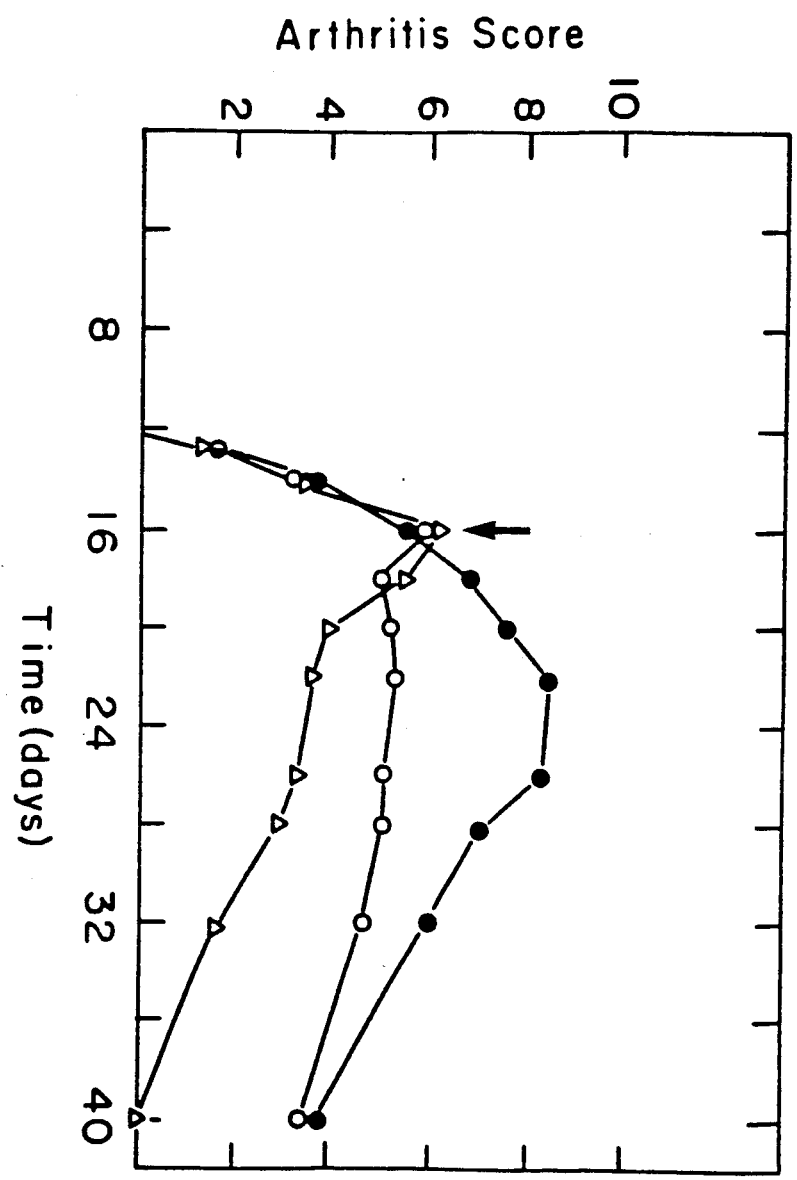

Rats were immunized with Mycobacteria, with water, and with AS in oil, see Table 4. The mycobacteria inocculated rats developed AA as expected, while the water and AS inoculated rats did not. After 35 days the rats were challenged with mycobacteria in oil to induce active AA. Rats that had suffered primary AA were resistant to a second bout; those inoculated with water only were susceptible to AA, whereas the AS inoculated rats were totally resistant to AA. Thus, the As fraction is arthritis suppressive, while not being arthritogenic. Moreover, AS can be used to activate cells of the A2 line to provide treatment of AA after its onset. (FIG. 2). The effective dosage varies, it is generally about 1 to 20 mg/kg, preferably about 2 to 10 mg/kg. This demonstrates that when AA was induced in rats by Mycobacteria, after 16 days, when arthritis had developed, some of the rats were inoculated intravenously with line A2 that had been activated with Mycobacteria or with the As fraction. The Mycobacteria treated A2 cells arrested the arthritis, while the AS treated A2 cells induced a full remission of the disease.

Table 5 demonstrates the proliferative responses of peripheral blood mononuclear cells of rheumatoid arthritis (RA) patients and controls, to mycobacterial antigens.

Several different species of mycobacteria were tested as to whether clones A2b and A2c recognized their differences. One of these, mycobacteria, M. vaccae was recognized in an in vitro proliferation test by the protective clone A2c but not by the arthritogenic clone A2b (Table 6). This finding indicated that M. vaccae was relatively rich in protective antigens and poor in arthritogenic antigens. Accordingly tests were carried out to evaluate the effect of M. vaccae on adjuvant arthritis (Table 7). The strain of M. vaccae used was that deposited at the National Collection of Type Cultures (NCTC) Central Public Health Laboratory, Colindale Avenue, London NW9 5HT on Feb. 13th 1984 under the number NCIC 11659. In the first experiments, rats were inoculated with M. vaccae and then a week later adjuvant arthritis was induced by immunizing the rats with M. tuberculosis. It was found that prior inoculation with M. vaccae prevented the development of arthritis. Thus M. vaccae is effective as a prophylactic vaccine against adjuvant arthritis.

Figure 3:
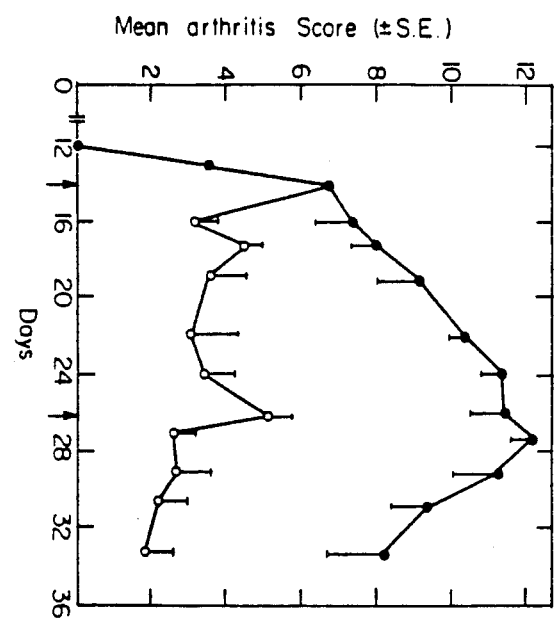

In the second series of experiments, adjuvant arthritis was first induced by immunization with M. tuberculosis and 3 weeks later, when all the rats were suffering from arthritis, some rats were inoculated with M. vaccae in oil, or with oil alone. Those receiving M. vaccae in oil had a remission in arthritis in several days while the control group of rats continued to suffer from severe arthritis (FIG. 3).

We have evidence that rheumatoid arthritis patients have T-lymphocytes that respond to the arthritogenic fraction of M. tuberculosis (Table 5), indicating that similar immunologic processes may occur in both adjuvant arthritis in rheumatoid arthritis.

According to the invention there are also provided compositions for the diagnosis of arthritic diseases and an assay for this purpose, based on the use of while mycobacteria or on the use of certain fractions thereof, obtained by the separation of mycobacteria. Such separation can be effected in a suitable solvent system, whereby there is obtained a soluble fraction and an insoluble one (precipitate). Each of these can be further fractionated and purified, until specifically active substances are obtained. Such fractions can be used for various types of assays for the above purpose, such as:

a 1. a lymphocyte proliferation test, or determination of any entity indicative of such proliferation;

a 2. indicative of the measure of lymphocyte activation are also changes which can be assayed by standard means so as to establish the presence and degree of lymphocyte activation: amongst these there may be mentioned:

a. production of lymphokines (such as interieukin-2 (1L-2);
  b. gamma interferon;
  c. migration inhibition factor (MIF);
  d. expression of membrane markers, such as 1L-2 receptor; peanut agglutination receptor.
  e. expression of enzymes such as heparanase;

b. determination of antibody titer in absolute terms or as a ratio of the values obtained by different fractions, said values or ratios being indicative of the presence or absence of the disease. Quantitative values obtained are of use in establishing the severity of the disease.

For carrying out such assays, there can be provided means in kit form, comprising one or more of the above defined fractions with suitable adjuvants and auxiliary components. Standardized kits with reference and calibration means are of value in the rapid and convenient determination of arthritic disease and its stage and/or severity.

LEGEND TO THE FIGURES

FIG. 1: Treatment of Adjuvant Arthritis (AA) Using Clone A2c:

AA was induced in Lewis strain rats by inoculation of MT. Sixteen and seventeen days later groups of 10 rats each were injected intraperitoneally with $2 \times 10^7$ cells of clone A2c (open circles) or central clone Cl a (closed circles). The rats were observed for the severity of arthritis on a clinical scale of 1 to 16. Upon examination 6 months later, recipients of clone A2c were free of disease while recipients of Cl a had severe ankylosis of the paws.

FIG. 2: Treatment of Adjuvant Arthritis by Injection of A2 Line Cells:

Adjuvant arthritis was induced in 30 Lewis rats by active immunization with complete Freund's adjuvant on day 0. On day 16, after arthritis had developed in all rats, they were divided into three groups. A control groups of 10 rats (solid circles) was not treated. A second group of 10 rats was treated by a single intravenous inoculation of $2 \times 10^7$ A2 line cells that had been activated using whole mycobacterial organisms (o). The third group of 10 rats was inoculated with A2 line cells that had been activated with the AS fraction (triangles). Severity of arthritis was assessed on a clinical scale of 1 to 16.

FIG. 3: Treatment of Adjuvant Arthritis by Injection of M. vaccae Cells

AA was induced in Lewis strain rats by immunization with M. tuberculosis and 2 and 4 weeks later, when all the rats were suffering from arthritis, some rats were inoculated with M. vaccae (1 mg.) in oil (in complete Freund's adjuvant) (open circles) or with the oil alone (solid circles). Severity of arthritis was assessed on a clinical scale of 1 to 16.

TABLE 1

Production and/or prevention of adjuvant arthritis (AA) by T-lymphocyte line A2 and clones A2b and A2c

| T-lymphocytes transferred ($2 \times 10^7$) | Recipient rats irradiated (750R) | Line-mediated arthritis | AA induced by MT 35 days after line transfer | | | |
|---|---|---|---|---|---|---|
| | | | % Incidence (no. rats) | Mean day of onset | Duration (days) | Clinical Arthritis |
| None | No | No | 89 (76) | 12.9 | 56 | Severe |
| | Yes | No | 81 (42) | 13.6 | 55 | Severe |
| A2 | No | No | 0 (69) | — | — | None |
| | Yes | Yes | 0 (38) | — | — | None |
| A2b | No | No | 91 (22) | 13.7 | 53 | Severe |
| | Yes | Yes | 93 (14) | 13.9 | 54 | Severe |
| A2c | No | No | 0 (15) | — | — | None |
| | Yes | No | 0 (15) | — | — | None |

Irradiated (750R) or non-irradiated Lewis rats were injected intravenously with $2 \times 10^7$ cells of line A2 or cloned sublines A2b or A2c-10. 35 days later active AA was induced by an intradermal injection of killed *Mycobacterium tuberculosii* organisms in oil (MT). Control groups consisting of irradiated or non-irradiated rats were injected with MT 35 days after irradiation.

TABLE 2

Responses of clones A2b and A2c to antigens

| Clone | In vivo effect | Response to antigens | | | |
|---|---|---|---|---|---|
| | | Whole mycobacteria | AP | AS | Cartilage proteoglycan |
| A2b | arthritogenic | + | + | − | + |
| A2c | protective, therapeutic | + | ± | + | + |

TABLE 3

Rabbit antibodies to AP or AS recognize joint cartilage

| Rabbit antiserum | Immunofluorescent staining of joint cartilage | Inhibition of staining with proteoglycan |
|---|---|---|
| normal | none | — |
| anti-AP | IgG | Yes |
| anti-AS | IgM | Yes |

TABLE 4

Active Immunization to AS Protects Rats against AA

| Primary Immunization | | Secondary challenge with mycobacteria in oil (MT) |
|---|---|---|
| Inoculum in oil 1 mg | % incidence of arthritis | % incidence of arthritis |
| Mycobacteria | 100 | 0 |
| Water | 0 | 100 |
| AS | 0 | 0 |

TABLE 5

Proliferative responses of peripheral blood mononuclear cells of rheumatoid arthritis (RA) patients and controls to mycobacterial antigens

| Group | No. of patients | Mean stimulation index | | | Significant response to* | | Ratio of responses |
|---|---|---|---|---|---|---|---|
| | | PPD | AP | AS | AP | AS | AP:AS |
| RA | 17 | 18.4 | 13.6 | 1.2 | 14/17 | 0/17 | 11 |
| Osteo-arthritis | 12 | 15.0 | 5.6 | 7.0 | 7/12 | 8/12 | 0.8 |
| Normal controls | 8 | 13.2 | 3.9 | 4.9 | 4/8 | 5/8 | 0.8 |

*Stimulation index > 2.0

TABLE 6

Therapeutic clone A2c recognizes *M. vaccae*, arthritogenic clone A2b does not.

| Clone | In vitro proliferation response ($H^3$—thymidine incorporation, cpm $\times 10^{-3}$) | | |
|---|---|---|---|
| | No antigen | *M. tuberculosis* | *M. vaccae* |
| A2b | 2 ± 1 | 6 ± 5 | 4 ± 1 |
| A2c | 1 ± 1 | 62 ± 6 | 60 ± 9 |

Clones A2b and A2c were assayed for their in vitro proliferative responses to *M. tuberculosis* or *M. vaccae* organisms in a standard test ($2.5 \times 10^4$ clone cells, $2 \times 10^6$ irradiated accessory cells and 2 ug of mycobacteria extract per well, $H^3$—thymidine incorporation for 18 h, after 24 h of incubation). Results are expressed as cpm.

TABLE 7

Treatment with *M. vaccae* induces resistance to adjuvant arthritis.

| Treatment | Arthritis induced by *M. tuberculosis* 3 months later | |
|---|---|---|
| | Incidence | Clinical grade |
| Oil (control) | 100% | Severe |
| *M. vaccae* in oil | 0% | 0 |

Groups of 13 Lewis rats were treated by intracutaneous inoculation of *M. vaccae* (1 mg) in oil (incomplete Freund's adjuvant) or by oil alone (control). Three months later, susceptibility to induction of adjuvant arthritis was tested by inoculating the rats with *M. tuberculosis* (1 mg) in oil.

We claim:

1. A method for the alleviation or treatment of arthritic disease which comprises administering to a patient suffering therefrom an effective amount of a composition comprising, as the active ingredient, a mycobacterium or a fraction thereof.

2. A method according to claim 1, wherein the mycobacterium is *M. vaccae*.

3. A method according to claim 1 wherein a dose of from about 2 mg to about 10 mg/kg weight of the patient is administered to the patient by injection.

4. A method according to claim 2 wherein the fraction is one obtained by fractionation of such mycobacteria in a suitable solvent system, and separating therefrom a soluble fraction used as the active component.

5. A method according to claim 4, wherein the solvent system for fractionation is an acetone/water mixture.

6. A method according to claim 5, wherein the solvent system used for fractionation is an acetone/water mixture of about 2/1 by volume.

* * * * *

UNITED STATES PATENT AND TRADEMARK OFFICE
CERTIFICATE OF CORRECTION

PATENT NO.   : 4,716,038
DATED        : December 29, 1987
INVENTOR(S)  : STANFORD ET AL It is certified that error appears in the above-identified patent and that said Letters Patent is hereby corrected as shown below:

In the heading, insert:

Assignee:  University College London and Yeda Research
           and Development Co. Ltd.

Signed and Sealed this

Seventh Day of February, 1989

*Attest:*

DONALD J. QUIGG

*Attesting Officer*     *Commissioner of Patents and Trademarks*